(12) United States Patent
Vogtherr et al.

(10) Patent No.: US 10,548,583 B2
(45) Date of Patent: Feb. 4, 2020

(54) TELESCOPING RETRACTOR HOLDER

(71) Applicant: Aesculap AG, Tuttlingen (DE)

(72) Inventors: Robert Vogtherr, Tuttlingen (DE);
Thomas Beck, Durchhausen (DE);
Pedro Morales, Tuttlingen (DE);
Dieter Weisshaupt, Immendingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/785,017

(22) PCT Filed: Apr. 24, 2014

(86) PCT No.: PCT/EP2014/058377
§ 371 (c)(1),
(2) Date: Oct. 16, 2015

(87) PCT Pub. No.: WO2014/174031
PCT Pub. Date: Oct. 30, 2014

(65) Prior Publication Data
US 2016/0051241 A1 Feb. 25, 2016

(30) Foreign Application Priority Data

Apr. 26, 2013 (DE) .................. 10 2013 104 300

(51) Int. Cl.
*A61B 17/02* (2006.01)
*A61B 17/00* (2006.01)

(52) U.S. Cl.
CPC ..... *A61B 17/0206* (2013.01); *A61B 2017/00991* (2013.01)

(58) Field of Classification Search
CPC .. A61B 2090/571; A61B 90/50; A61G 13/101
See application file for complete search history.

(56) References Cited

U.S. PATENT DOCUMENTS 3,394,700 A * 7/1968 Yamamoto ............. A61B 17/02
600/233
3,638,972 A 2/1972 Poletti
(Continued)

FOREIGN PATENT DOCUMENTS

DE 3717915 12/1987
DE 29804127 5/1998
(Continued)

OTHER PUBLICATIONS

German Search Report for German Application No. 10 2013 104 300.3 dated Jan. 14, 2014, including partial translation.
(Continued)

*Primary Examiner* — Jacqueline T Johanas
(74) *Attorney, Agent, or Firm* — RatnerPrestia

(57) ABSTRACT

A telescoping retractor holder includes a length-adjustable support, the one end section of which can be supported on an operating table, and including a retractor lever, the one, distal end of which includes a retractor receptacle adapted to releasably grip a retractor, and the other, proximal end section of which can be operatively connected in a supporting manner to the other free end section of the telescoping support, preferably by way of a detachable connecting means, for the application of a lever force.

14 Claims, 9 Drawing Sheets

(56) References Cited

U.S. PATENT DOCUMENTS

| | | | |
|---|---|---|---|
| 3,638,973 A * | 2/1972 | Poletti | A61B 17/02 137/583 |
| 3,643,655 A | 2/1972 | Peronti | |
| 3,710,783 A | 1/1973 | Jascalevich | |
| 3,810,462 A * | 5/1974 | Szpur | A61B 17/02 403/59 |
| 3,971,538 A * | 7/1976 | Marvich | A61G 13/10 248/278.1 |
| 4,051,844 A | 10/1977 | Chiulli | |
| 4,099,521 A | 7/1978 | Nestor et al. | |
| 4,116,232 A | 9/1978 | Rabban | |
| 4,155,355 A * | 5/1979 | Yamamoto | A61B 17/0293 600/233 |
| 4,380,999 A * | 4/1983 | Healy | A61B 17/02 248/297.31 |
| 4,616,632 A | 10/1986 | Wigoda | |
| 4,829,985 A | 5/1989 | Couetil | |
| 5,000,163 A * | 3/1991 | Ray | A61B 17/0293 24/490 |
| 5,025,779 A | 6/1991 | Bugge | |
| 5,109,831 A * | 5/1992 | Forrest | A61B 17/02 600/228 |
| 5,372,147 A | 12/1994 | Lathrop, Jr. et al. | |
| 5,520,608 A | 5/1996 | Cabrera et al. | |
| 5,573,495 A | 11/1996 | Adler | |
| 5,603,689 A | 2/1997 | Lucini | |
| 5,746,741 A | 5/1998 | Kraus et al. | |
| 5,752,954 A | 5/1998 | Mata et al. | |
| 5,846,194 A * | 12/1998 | Wasson | A61B 17/0281 600/228 |
| 5,882,299 A | 3/1999 | Rastegar | |
| 5,897,087 A | 4/1999 | Farley | |
| 5,908,382 A | 6/1999 | Koros et al. | |
| 5,967,974 A * | 10/1999 | Nicholas | A61B 17/0293 600/228 |
| D425,620 S | 5/2000 | Koros et al. | |
| 6,154,901 A * | 12/2000 | Carr | A61G 13/12 5/601 |
| 6,228,026 B1 * | 5/2001 | Rullo | A61B 17/02 600/227 |
| 6,241,659 B1 | 6/2001 | Bookwalter et al. | |
| 6,322,501 B1 | 11/2001 | Fernot | |
| 6,386,786 B1 | 5/2002 | Perlman et al. | |
| 6,416,468 B2 | 7/2002 | Deckman et al. | |
| 6,488,621 B1 | 12/2002 | Rullo et al. | |
| 6,689,053 B1 | 2/2004 | Shaw | |
| 6,808,493 B1 | 10/2004 | Bookwalter et al. | |
| 7,131,955 B2 * | 11/2006 | Price | A61F 5/04 602/36 |
| 7,507,202 B2 | 3/2009 | Schoellhorn | |
| 7,887,481 B2 * | 2/2011 | Lamadon | A61B 17/02 600/201 |
| 8,231,528 B1 * | 7/2012 | Friedrich | A61B 17/02 600/228 |
| 9,078,635 B2 * | 7/2015 | Menendez | A61B 17/02 |
| 9,532,842 B2 * | 1/2017 | Chauvette | A61F 5/3761 |
| 2002/0026101 A1 * | 2/2002 | Bookwalter | A61B 17/0293 600/231 |
| 2002/0161446 A1 * | 10/2002 | Bryan | A61B 17/02 623/17.15 |
| 2003/0149429 A1 | 8/2003 | Ferrante et al. | |
| 2003/0178027 A1 * | 9/2003 | DeMayo | A61G 13/12 128/845 |
| 2006/0253109 A1 * | 11/2006 | Chu | A61B 17/0206 606/1 |
| 2007/0185376 A1 | 8/2007 | Wilson et al. | |
| 2008/0172791 A1 * | 7/2008 | Walczyk | A61G 13/12 5/623 |
| 2009/0247819 A1 * | 10/2009 | Wilson | A61B 17/02 600/102 |
| 2009/0287062 A1 * | 11/2009 | Farley | A61B 17/0206 600/231 |
| 2010/0087819 A1 | 4/2010 | Mullaney | |
| 2010/0292542 A1 * | 11/2010 | Kanekasu | A61B 90/57 600/231 |
| 2010/0312069 A1 * | 12/2010 | Sutherland | A61B 90/35 600/245 |
| 2011/0270042 A1 * | 11/2011 | Giulianotti | A61B 17/02 600/228 |
| 2012/0283522 A1 * | 11/2012 | Qian | A61B 17/02 600/231 |
| 2013/0006060 A1 | 1/2013 | Caner | |
| 2013/0023735 A1 * | 1/2013 | Brown | A61B 17/02 600/229 |
| 2014/0296650 A1 | 10/2014 | Weisshaupt | |
| 2017/0119436 A1 * | 5/2017 | Farzadfard | A61B 17/66 |
| 2017/0128058 A1 | 5/2017 | Barnett et al. | |
| 2018/0168842 A1 * | 6/2018 | Hunter, Jr. | A61F 5/04 |

FOREIGN PATENT DOCUMENTS

| | | |
|---|---|---|
| DE | 10325393 | 1/2005 |
| DE | 10325393 B3 | 1/2005 |
| DE | 102009021224 A1 | 11/2010 |
| DE | 102011117484 | 5/2013 |
| EP | 0931509 | 4/2005 |
| EP | 2119400 A1 | 11/2009 |
| WO | 2012159088 | 11/2012 |
| WO | 2013060581 | 5/2013 |

OTHER PUBLICATIONS

International Search Report dated Sep. 18, 2014 for International Application No. PCT/EP2014/058377.

Notification of Reasons for Rejection for Japanese Application No. 2016-509471, dated Nov. 28, 2017, including English translation, 6 pages.

International Search Report for Internationnal Application No. PCT/EP2012/070277, dated Dec. 12, 2012, 3 pages.

* cited by examiner

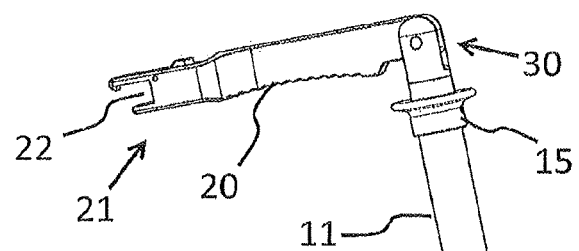
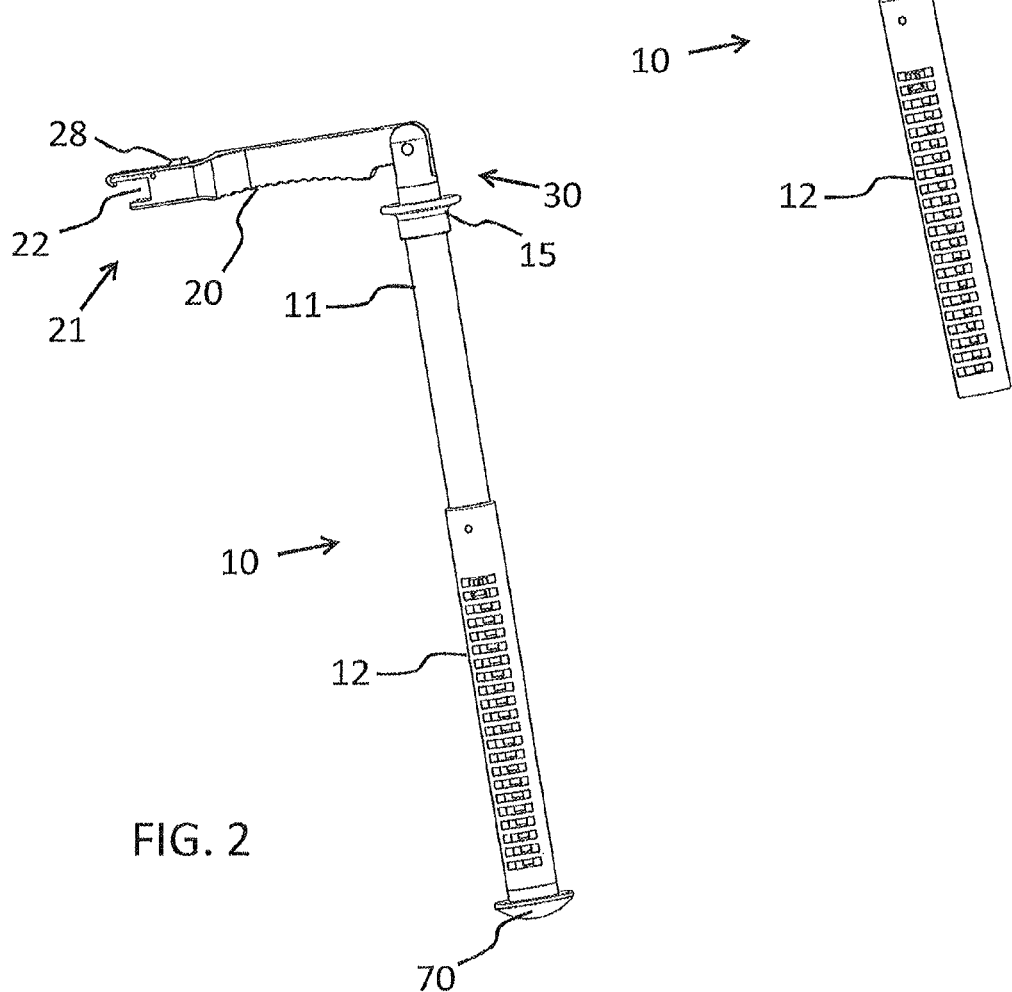

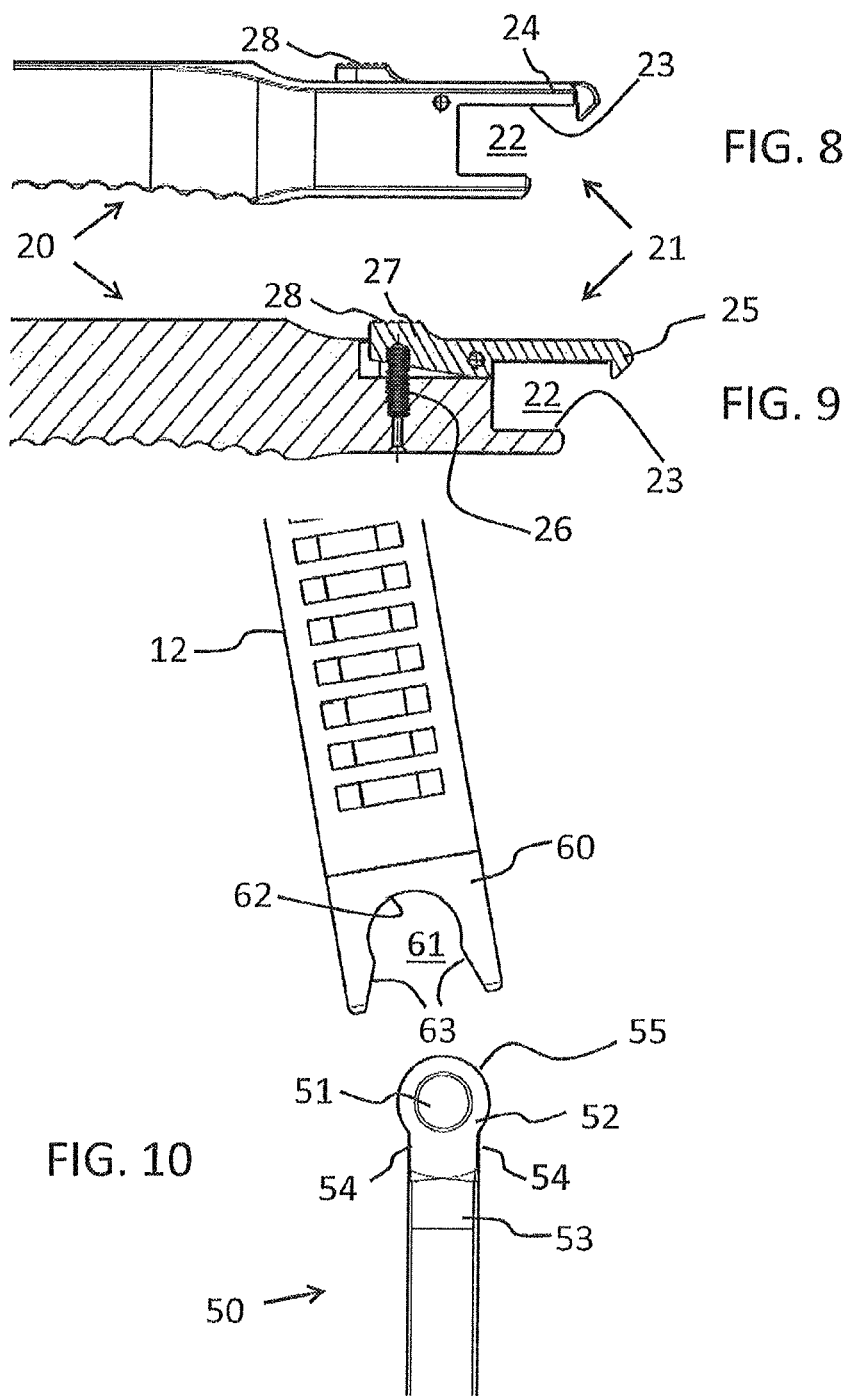

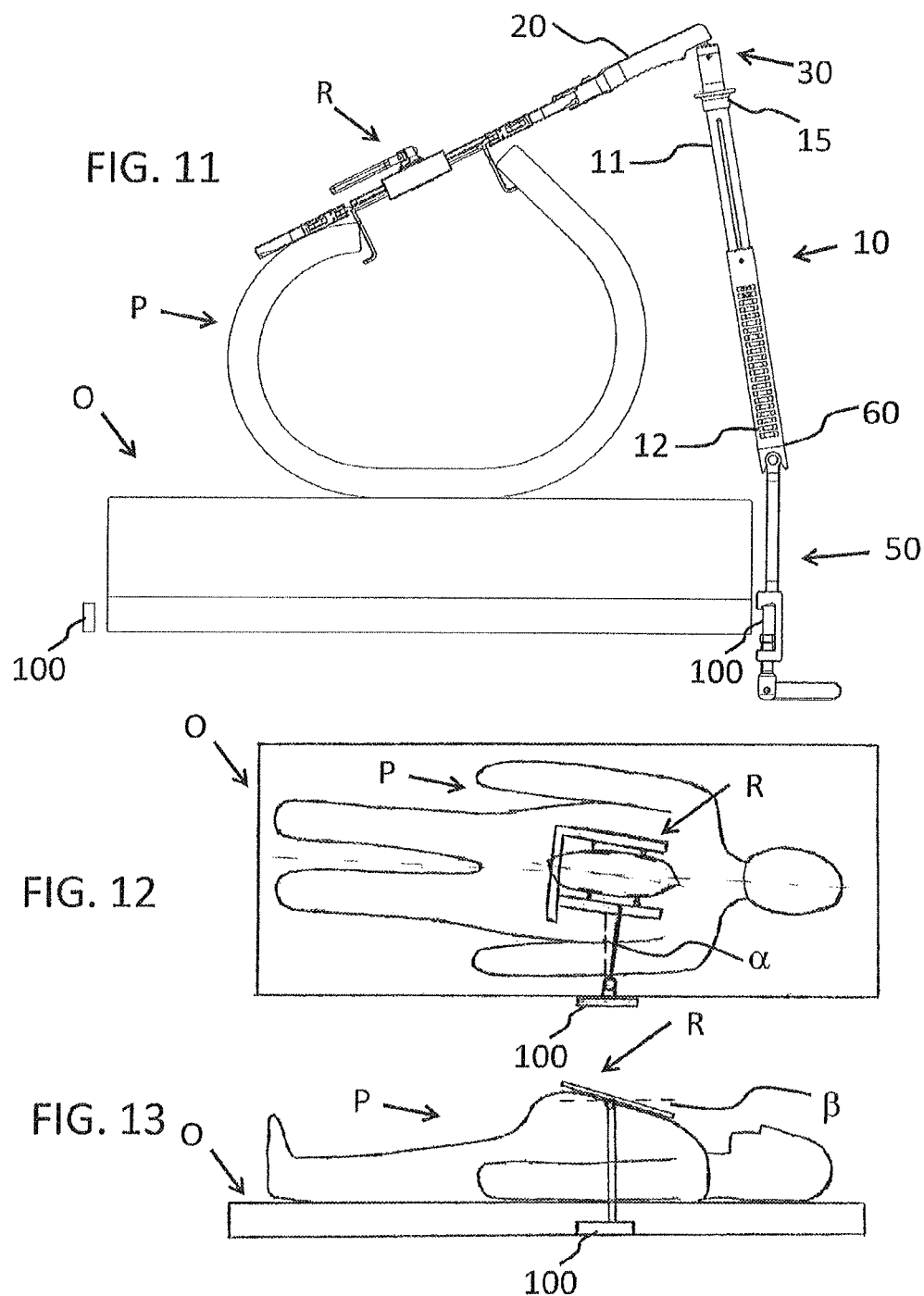

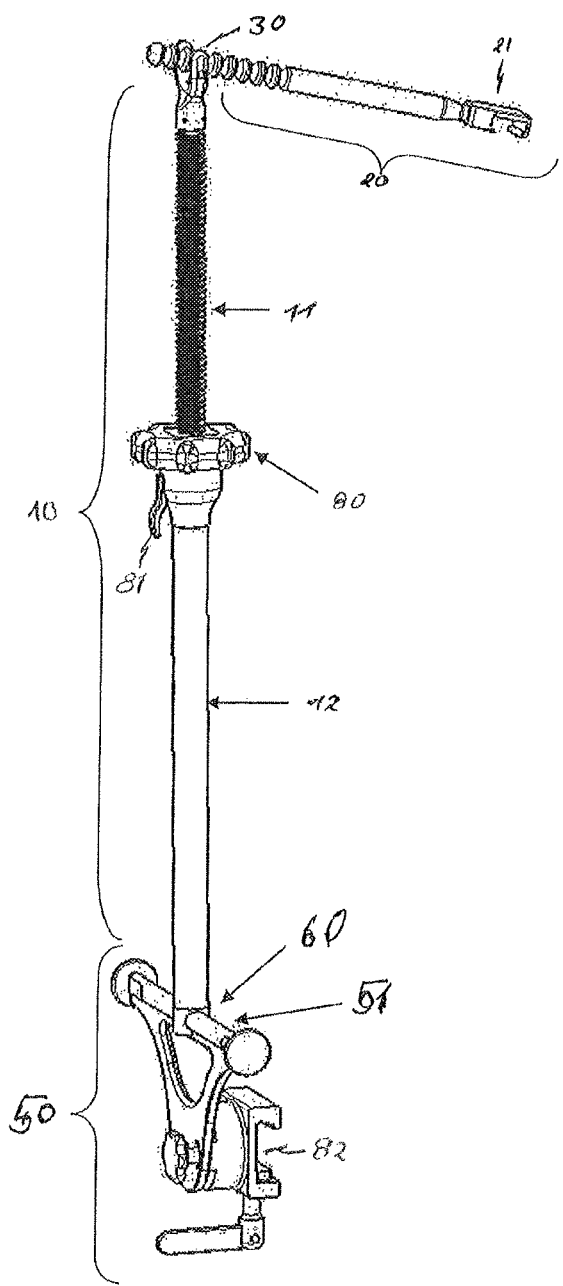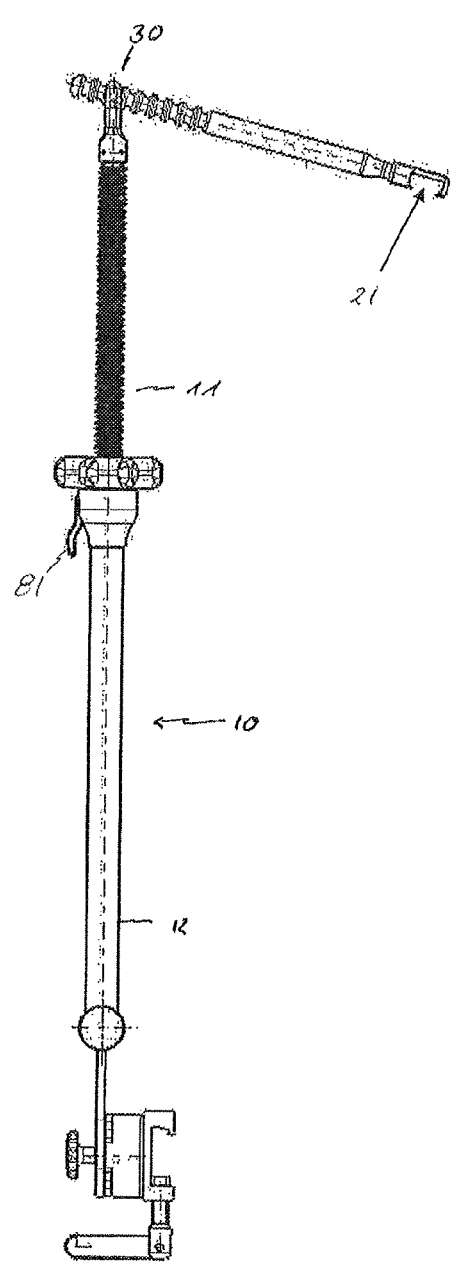

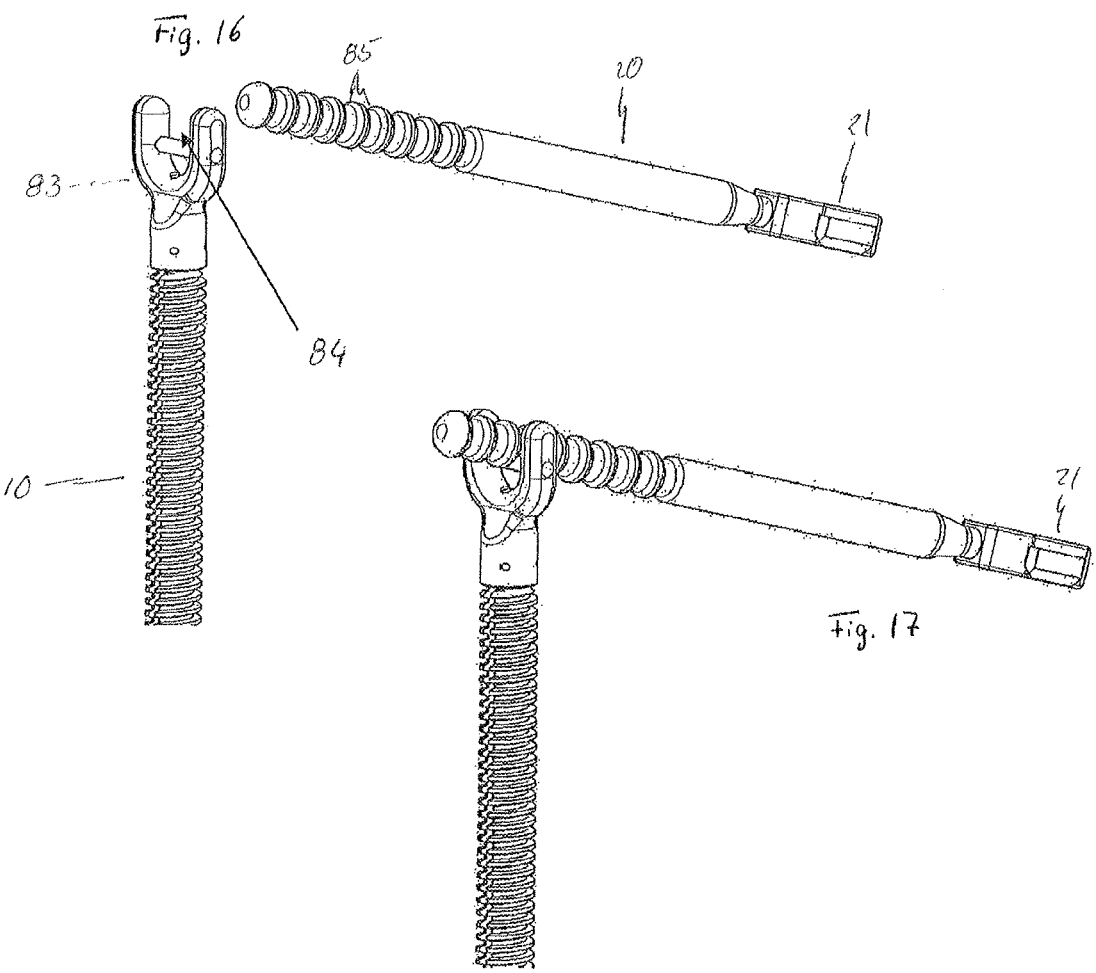
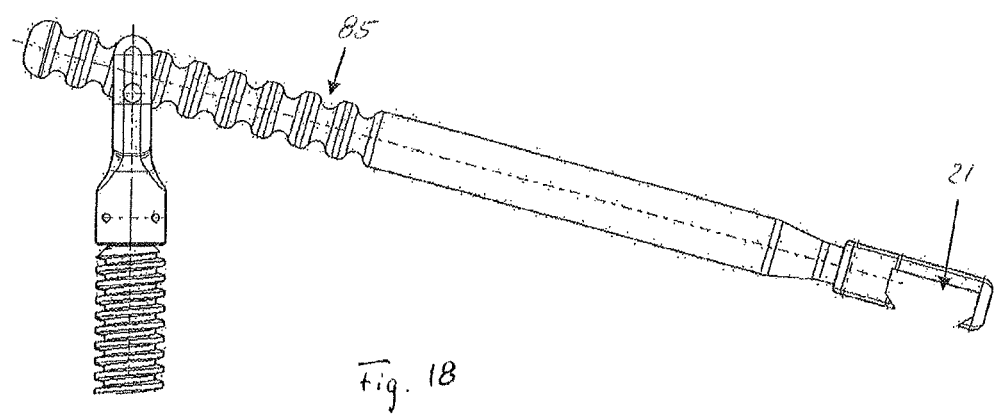

TELESCOPING RETRACTOR HOLDER

RELATED APPLICATIONS

This application is the U.S. National Phase entry of International Application No. PCT/EP2014/058377, filed Apr. 24, 2014. Moreover, this application is related to and claims the benefit of priority of German Application No. DE 10 2013 104 300.3, filed Apr. 26, 2013. The contents of International Application No. PCT/EP2014/058377 and German Application No. DE 10 2013 104 300.3 are incorporated by reference herein and for all purposes.

FIELD

The present invention relates to a telescoping retractor holder and, more particularly, to a surgical lifting device with one-handed operation for raising a retractor, for example for the dissection of mammary arteries.

BACKGROUND

Many cardiac surgery procedures require the sternum of the patient to be cut longitudinally and the sternal halves, together the adjoining ribs, to be spread apart so as to allow the surgeon to work on the heart. Retractors are used to spread this surgical opening. If the procedure includes treatment of circulatory disorders of the coronary heart vessels, what is known as a bypass operation is carried out. The establishment of what is known as a mammary artery bypass is one of the most common surgical methods. In such bypass operations, a path is created around a section of a narrowed coronary artery. The internal mammary artery (IMA), which is used as the bypass vessel for this purpose, runs along the inside of the thorax. A portion of this artery is dissected free by the surgeon, and the end is sutured to a coronary artery.

Normally the left internal mammary artery (LIMA) is used, but often the right artery (RIMA) is also used. So as to be able to provide the surgeon with sufficient operating space and adequate visibility for this work, a lifting system is needed, which is able to vertically raise and support one half of the cut sternum, together with the adjoining ribs.

A wide variety of systems of this type is known from the prior art. A first type of lifting systems, which are disclosed in the patent specifications EP 0 931 509 B1 or U.S. Pat. No. 6,416,468 B2, for example, is based on a conventional retractor comprising an adaptor device, which is mounted on the retractor and raises the same on one side. In patent specification EP 0 931 509 B1, the raising is implemented by way of a screw having support plates and a thread pivotably attached to the retractor. The lifting system is clamped or screwed to the retractor. According to patent specification U.S. Pat. No. 6,416,468 B2, the screw and the thread are replaced by a detent mechanism; however, the fundamental operating principle is the same. To raise one side of the sternum, the support plate is pressed against the ribs, whereby the side of the sternum on which the lifting system is located is pulled outward.

The second type of lifting systems is very similar and operates with special blades on an otherwise likewise conventional retractor. Instead of using an adapter device, the principle of the above-described raising is achieved by way of a special blade here, which is attached to the retractor frame in an articulated manner, and a spacer element. The spacer element is used to set the distance between the pivoting side of the special blade and the retractor frame, and thus the raising of the corresponding sternal half. Such systems are described in the documents U.S. Pat. No. 5,025,779 A and DE 10 325 393 B3.

Also known are pure mammary artery retractors, which are not used for normal sternal spreading, but only for carrying out the dissection of the mammary artery. Patent specification DE 3 717 915 C2 describes such a retractor, which functions without a separate lifting device. A blade located at a fixed angle with respect to the toothed rack of the retractor is clamped into the sternal half which is not raised, so that the retractor becomes obliquely positioned with respect to the normal thoracic surface of the patient when the sternum is spread by way of the pinion, and the other sternal half is pulled upward by way of special blades designed as claws.

One technique that differs substantially from the three above-described variants is that of raising one sternal half by way of cables or pull rods in conjunction with an external attachment means. This technique can be found in the published prior art U.S. Pat. No. 6,488,621 B1 or U.S. Pat. No. 6,689,053 B1. Here, only the desired sternal half is raised by way of hooks, which are provided on a cable or a pull rod, wherein the tractive force is absorbed by a fastening element, such as a frame or a rod, which is fastened to the side of the operating table, for example.

In all conventional devices of this type, the user, which is to say the surgeon, must be prepared for several drawbacks, which prevent an optimal process on the one hand, and an ideal result of the surgical procedure on the other hand.

The greatest disadvantage are the high forces which arise when the sternum is raised and the adjoining ribs are spread apart, and which are usually distributed to the body of the patient through supporting elements. The sternal half in question becomes exposed in this process, which is to say bent open outward; however, the force required to do so is distributed to the adjoining ribs on the same side of the body. Due to various lever arms, this results in extremely high forces being exerted on the patient. This, in turn, poses a high risk of partial sternal fractures, fractures of the ribs, and damage to neural pathways.

The technique of external attachment forms one exception, since the force required to expose the sternal half is distributed to the attachment system here, and not to the patient. However, this technique does not provide adequate visibility since only vertical raising of one sternal half takes place, and no adequate opening on the horizontal axis is provided. Due to the absence of horizontal forces, it is also not possible to use regular blades here; rather, claw-shaped hooks are needed, which are seated against the sternum in a highly localized manner and can cause substantial fractures. In addition, such systems are very tall above the operating level and consequently interfere with many work flows of the surgical staff.

Another point of criticism is the extremely cumbersome repositioning of the lifting systems to the other side in the case where two mammary arteries (left and right) require consecutive dissection. This repositioning is still relatively simple in devices that are adapted to the retractor; however, an assistant will usually have to help the surgeon. In contrast, retractors comprising special blades must be completely removed from the surgical opening and repositioned, which represents not only an interruption of the surgical process, but also a relatively critical moment since the surgeon no longer has access to the heart when the retractor is removed.

In systems comprising an external fastening rod, which is mounted to the operating table, there is almost no practical way to reposition the system to the other side. The reason behind this is that all regions located vertically below the surgical area are considered non-sterile. A mounting on the operating table will thus be in the non-sterile region and cannot be detached and relocated to another point. Likewise, work steps that must be carried out during surgery in this region, such as loosening a clamped connection, are impermissible.

SUMMARY

It is the object of the present invention to create a retractor holder that makes it possible to expose a sternal half and establish an adequate horizontal sternum opening, while posing the least stress for the patient. It is a further object of the present invention to create a retractor holder that can be operated with only one hand. It is still another object of the present invention to create a retractor holder that can either be easily repositioned from one side of the operating table to the other side using one hand or that renders such repositioning entirely unnecessary.

The object of the present invention is achieved by a telescoping retractor holder as described herein.

According to one aspect of the present invention (which may optionally be claimed independently), a telescoping retractor holder is created, comprising a support, preferably a telescoping support rod, more preferably having an inner pipe, an outer pipe, and a locking mechanism for fixing a freely/individually selected support rod length, and comprising a retractor lever, preferably a retractor rod, which at the distal end thereof comprises a retractor receptacle adapted to releasably grip or adapt a retractor, and which at the proximal end thereof is held or supported, preferably loosely, on the telescoping support rod by way of a detachable connecting means. The telescoping support rod can be supported on an operating table and comprises an actuating mechanism, by way of which the locking mechanism can be transferred from a first position, in which the support rod length is fixed (the inner pipe and the outer pipe of the telescoping support rod are held non-displaceably with respect to each other), into a second position, in which the support rod length is adjustable (the inner pipe and the outer pipe of the telescoping rod can be moved relative to each other in the longitudinal direction of the pipes).

In this embodiment, the retractor holder according to the invention is held in a substantially upright position when used on the patient in that the retractor is fastened to the sternum of the patient and the retractor receptacle grips the retractor. In this way, a defined position of the retractor holder is created by the bearing forces of the sternum, the support of the telescoping support rod, and the lengths of the telescoping support rod and of the retractor rod. The substantially upright position of the retractor holder refers to the then substantially vertical position of the telescoping rod. In other words, the (longitudinally cut) sternum is spread or pried open by way of the retractor as is customary for the function of the same (in the manner of a known mammary artery retractor), wherein the retractor is subsequently moved or pivoted by way of the retractor rod by longitudinally adjusting (extending) the support rod. The retractor is thus raised on one side (on the side of the support rod) together with the corresponding sternal half, until optimal visibility of the internal mammary artery for the surgeon has been established.

The length of the telescoping support rod can preferably be varied by releasing the locking mechanism with the aid of the actuating mechanism, setting the length of the telescoping support rod by raising or lowering the actuating mechanism, and subsequently releasing the actuating mechanism, so that the locking mechanism locks the set length (positions of the inner pipe and of the outer pipe of the telescoping support rod with respect to each other). In the simplest case, which is initially shown here, the telescoping support rod is supported on the surface of an operating table. Indentations may be provided in the operating table so as to prevent the telescoping rod from sliding.

According to another aspect of the present invention, which may optionally be claimed independently, the telescoping support rod can be supported on the operating table in an articulated/hinge-like manner. This means that the telescoping support rod need not be positioned exactly perpendicularly with respect to the operating table, but the position thereof may be adjusted to the further geometry and the support conditions of the retractor on the sternum of the patient. Essentially, a rotation of the retractor holder or of the telescoping support rod with respect to the operating table about a longitudinal axis of the operating table will take place, whereby the contact point between the telescoping support rod and the retractor rod moves toward the patient and away from the same. If, however, the retractor is spread further while it is held by the retractor rod, the sternum will automatically become positioned obliquely with respect to the frontal plane during lifting, and more particularly with the caudal region higher than the cranial region, since the caudal pairs of ribs, among other things, in humans are longer and more flexible than the cranial pairs. This difference in height will vary depending on the exposure of the sternum and will result in a rotation of the retractor with respect to the horizontal. The telescoping support rod can thus also rotate about the transverse axis of the operating table, at least to a certain degree, either due to an articulated mounting in this direction or a certain degree of play in the fastening, or the rotation is absorbed by the reactor rod, which has a corresponding degree of freedom.

According to another aspect of the present invention, which may optionally be claimed independently, the retractor rod of the telescoping retractor holder is freely telescoping. Freely telescoping means here that no locking mechanism is provided in the retractor rod, and therefore the rod can freely vary in length at any time. Such a telescoping retractor rod can be used to fasten the telescoping support rod to the operating table in a substantially non-articulated manner, and when the telescoping support rod is lengthened, the retractor rod is also lengthened, so that the patient is not raised at the sternum, but only one side of the sternum is raised by way of the retractor and the retractor holder. The aforementioned degree of freedom for a rotation of the retractor with respect to the horizontal may then also be provided in the telescoping device of the retractor rod, in that the freely telescoping retractor rod is not able to absorb or transfer torsional forces.

As an alternative or in addition to the telescoping retractor rod, however, it is also possible to design the detachable connecting means between the retractor rod and the support rod in such a way that the effective retractor rod length between the support rod and the retractor receptacle can be varied. For example, the retractor rod can comprise a number of longitudinally spaced points of action/points of engagement in the region of the connecting means, at which the retractor rod can be detachably engaged in/bear on the support rod. In addition, the connecting means may be configured so as to allow a longitudinal displacement of the retractor rod held thereon.

According to a further aspect of the present invention, which may optionally be claimed independently, the actuating mechanism is arranged in the region of the connecting means with the retractor rod. The connecting means is essentially always located in the plane spanned by the retractor. The actuating mechanism is thus likewise located in this region, and consequently is always located in the sterile region. The surgeon may thus operate the retractor holder without first having to carry out a sterilization again.

According to another aspect of the present invention, which may optionally be claimed independently, the inner pipe of the telescoping support rod can be supported on an operating table, one end of the outer pipe of the telescoping support rod is operatively connected to the retractor rod by way of the detachable connecting means, and the actuating mechanism is arranged in the region of the other end of the outer pipe. In this case, the actuating mechanism is arranged slightly lower than in the above-described case; however, it is still located in a region that may be deemed to be sterile.

According to another aspect of the present invention, which may optionally be claimed independently, the retractor receptacle is adapted to positively grip or adapt a retractor. In this way, it is easy to transfer the forces and moments of the retractor to the retractor holder, and vice versa.

According to a further aspect of the present invention, which may optionally be claimed independently, the retractor receptacle is a substantially U-shaped recess, into which a frame of a retractor can be inserted, so that the same makes a least partial contact with the inside wall of the recess on at least two sides. The distal end of an elastically preloaded tongue, serving as a detent means, comprises a locking protrusion, which is adapted to be seated against a retractor frame after the same has been inserted and thereby establish a positive fit with the retractor frame. In the simplest case, the U-shaped recess is seated against three sides of a retractor component/retractor frame, and the locking protrusion is seated against the fourth side of the retractor component/retractor frame, so as to prevent the same from sliding out of the retractor receptacle. The gripped retractor component does not have to be right-angled. It is merely advantageous if the gripped retractor component is not rotation-symmetrical. In this case, a non-positive connection would have to be established between the retractor and the retractor receptacle, which is easy to do, but makes operating the same by the surgeon during surgery more complicated.

According to a further aspect of the present invention, the tongue is rotatably attached on one side of the recess and preloaded by an elastic component so that the distal end of the tongue, comprising the locking protrusion, pushes toward the recess. This corresponds to an advantageous arrangement since the surgeon can detach the retractor receptacle from the retractor by gripping the retractor rod with one hand and, for example, using the thumb of the same hand to press the proximal end of the tongue so as to overcome the undercut of the locking protrusion at the distal end of the tongue with the side of the retractor component which faces away, so as to detach the retractor from the retractor receptacle. However, two opposing tongues, which behave mirror-symmetrically with respect to each other, are also conceivable. A tongue which is inserted into a retractor component and the distal end of which is preloaded away from the U-shaped recess is conceivable as well.

According to a further aspect of the present invention, the elastic component is a compression spring, which presses the proximal end of the tongue. In this case, the elastic component can be arranged in the region of the base of the U-shaped recess. This arrangement is also suited for a retractor receptacle comprising two tongues, wherein one compression spring can be provided for each tongue, or a shared compression spring may be provided.

According to a further aspect of the present invention, the proximal end of the tongue comprises an actuating protrusion for releasing a retractor from the retractor receptacle. This makes it easier for the surgeon to feel the tongue, and also makes it easier to press the proximal end of the tongue. The tongue can thus have a smaller design, since the recess for accommodating the proximal end of the tongue does not have to be configured to accommodate the thumb or another actuating finger of the surgeon.

According to a further aspect of the present invention, which may optionally be claimed independently, the detachable connecting means, which connects the retractor rod to the telescoping support rod, is a hinged joint, preferably comprising easily removable cotter bolt as a pivot element. Such a hinged joint is the simplest form of a quick-release joint and is advantageous in the retractor holder according to the invention in particular when the retractor rod has a freely telescoping design and does not transfer torsional forces. Instead of using the removable cotter bolt, there is also the option to design the bearing lugs on the side of the retractor rod so as not to be entirely closed, but to be open, in the manner of a clamp, which can then simply be elastically pressed onto the pivot pin and can be easily pulled off the pivot pin in the same manner.

According to a further aspect of the present invention, the detachable connecting means, which connects the retractor rod to the telescoping rod, is a ball (head) joint. According to this aspect, the retractor rod may be torsionally rigid since the torsional forces are not transferred by the ball joint.

According to a further aspect of the present invention, the detachable connecting means can comprise at least one, preferably multiple, longitudinally spaced undercuts/notches/grooves and the like on the retractor rod, which selectively cooperate with a holding edge or cross pins/pivot pins at the free end of the support rod (by simple abutment), and thereby prevent inadvertent longitudinal displacement of the reactor rod on the support rod. There is also the option to provide the connecting means in the form of a clamp (pipe clip, and the like), which is held pivotably and/or rotatably on the support rod and optionally holds the retractor rod in a frictionally engaged manner.

According to a further aspect of the present invention, which may optionally be claimed independently, the actuating mechanism is a ring, which can be moved relative to the telescoping rod so as to transfer the locking mechanism from the first position into the second position. A ring that can be displaced with respect to the pipe, on which it is provided, in the longitudinal direction of this pipe is advantageous for this purpose, so as to release the locking mechanism. However, the actuating mechanism may also take on a variety of other forms, for example as an actuating button or a lever, which is pressed so as to release the locking mechanism, or as a ring or another component, which is rotated relative to the particular pipe so as to release the locking mechanism, either about the axis of the pipe or in another direction. The support rod may also be designed as a spindle rod or a toothed rack, wherein the actuating mechanism in the case of a spindle is an adjusting screw, the rotation of which displaces the spindle (inner pipe) along the spindle cylinder (outer pipe). If a toothed rack is provided, the actuating mechanism could conceivably be a crank mechanism.

According to a further aspect of the present invention, the end section of the telescoping support rod which is located opposite the detachable connecting means comprises a substantially U-shaped fastening receptacle so as to be place the same from above onto an operating table rail. In the simplest case, this fastening receptacle is simply placed over an operating table rail, without creating any kind of positive fit or close contact. In this way, the telescoping rod can rotate sufficiently with respect to the operating table rail in all directions and thus adapt to the force and moment conditions of the system.

According to a further aspect of the present invention, the cross-section of the fastening receptacle is adapted to a cross-section of an operating table rail, so as to make at least partial contact on two side walls of the operating table rail when the fastening receptacle is placed on. The fastening receptacle is attached to the telescoping rod by way of a joint connection. The rotation of the telescoping rod with respect to the operating table rail is used to ensure that no excessive forces are transferred from the sternum to the retractor, and subsequently to the retractor holder and the operating table, or in the opposite direction, so as to reliably avoid injury to the sternum or the surrounding tissue of the patient. The most important rotation of the telescoping rod with respect to the operating table is a rotation about the longitudinal axis of the operating table. The rotations in other directions are primarily created as a result of incorrect positioning of the patient on the operating table, cuts through the sternum that are not straight, and further spreading of the sternum. However, the magnitude of these rotations is such that these can be absorbed by the various supporting systems by way of play. Moreover, the surgeon always has the option to adapt the position of the supporting point for the telescoping rod along the longitudinal body axis of the patient in such a way that the described inadvertent rotations are minimized.

According to a further aspect of the present invention, the joint connection between the telescoping rod and the fastening receptacle is designed so that a rotational movement between the telescoping rod and the fastening receptacle is only possible in a predetermined angular range. This angular range is sufficiently large to allow the changes in length of the telescoping rod from a maximal length to a minimal length, or vice versa, to be carried out without the angle being limited. Rather, this angular limitation serves to prevent the retractor receptacle from tilting and entering the non-sterile region when the surgeon has already, directly or indirectly, fastened the fastening receptacle to the operating table rail, but has not yet fastened the retractor receptacle to the retractor.

In this state, the retractor holder may tilt away from the patient if the angle is not limited, and thereby may tilt into the non-sterile region. If the angle is limited, the holder can tilt away only by a predetermined angle, and the region of the retractor holder on which the surgeon grips and actuates the retractor holder remains in the sterile region. This makes the use of such a retractor holder even safer.

According to still another aspect of the present invention, which may optionally be claimed independently, the telescoping retractor holder comprises at least one fastening mechanism, which comprises a fastening rail and is adapted to be detachably fastenable to an operating table rail. The end section of the telescoping support rod located opposite the detachable connecting means comprises a fastening receptacle, which can be placed or pushed onto the fastening rail. If the retractor holder is to be supported on an operating table rail or fastened thereto, there is the problem that these operating table rails are not provided continuously along the entire length of the operating table. The reason for this is, among other things, that operating tables are segmented so as to enable a wide variety of settings for the patient and the surgery. Moreover, the operating table rails are generally covered by sterile drapes and consequently not visible. If the retractor holder is displaced along the operating table rail, it is possible to inadvertently damage cables/lines/and the like located thereon. So as to solve these problems, the telescoping retractor holder according to the invention comprises the above-described fastening mechanism, which is designed as a separate unit and, in turn, can be fastened to the operating table rail, and provides a separate fastening rail (above the surgical drapes and consequently visible to the surgeon), on which the telescoping support rod of the telescoping retractor holder can be supported. The term 'pushing on' here denotes a pushing of the fastening receptacle on the fastening rail in the longitudinal direction of the same.

According to a further aspect of the present invention, the fastening rail of the separate fastening mechanism has a cross-section that is composed of a substantially circular area and a further area. The fastening receptacle of the telescoping support rod has a recess having an inside wall and two side walls, wherein the cross-section of the recess substantially corresponds to the cross-section of the fastening rail. The inside wall of the recess establishes at least one undercut together with the fastening rail when the fastening receptacle is pushed on, the undercut being able to transfer tensile forces from the telescoping rod to the fastening rail. Moreover, the side walls of the recess are spaced from the lateral surfaces of the further area of the cross-sectional area of the fastening rail and oriented in such a way that rotation of the telescoping rod relative to the fastening rail is limited to a predetermined angular range. The cross-section of the fastening rail, composed of a rotation-symmetrical component and a further not rotation-symmetrical component, which is to say at least not rotation-symmetrical with respect to the same center as the first component, and the associated fastening receptacle are used to allow a rotation of the telescoping rod with respect to the fastening rail within a certain angular range, while preventing rotation beyond that. The simplest assembled form of this type is the shape of a keyhole, consisting of a circular area and a circular segment area connecting thereto, which is not entirely rotation-symmetrical.

According to a further aspect of the present invention, the fastening receptacle is arranged at one end of the telescoping support rod. In this way, the lower pipe of the telescoping support rod and the fastening receptacle can be designed in one piece.

According to a further aspect of the present invention, the retractor rod is detachably/loosely operatively connected to the inner pipe of the telescoping rod, the actuating mechanism is preferably provided on the inner pipe of the telescoping support rod, and the fastening receptacle is preferably provided on a side wall of the outer pipe of the telescoping support rod. A fastening receptacle that is provided on the side of the outer pipe of the telescoping support rod allows the length of the telescoping support rod to be increased, without the height of the system over the operating table increasing, which would impede the surgeon, for example limit the view or freedom of movement. The greater length of the telescoping support rod is in particular advantageous when not only the side of the sternum on which the retractor holder is located is to be raised, using the telescoping retractor holder, by increasing the length of the telescoping support rod, but when the other sternal half is to be raised as well by reducing the length of the telescoping support rod. The retractor is in each case supported on the sternal half which is not raised, which is easily possible, since the ribs are considerably easier to bend apart than to press in. However, so as to achieve an adequate length of the telescoping support rod without the height of the system over the operating table becoming so tall that the surgeon is impeded, it is advantageous to extend the telescoping support rod under the operating table rail. So as to then still be able to fasten the telescoping support rod on the operating table rail, the fastening receptacle must be attached to the side of the telescoping support rod.

According to a further aspect of the present invention, the telescoping support rod comprises at least one further center pipe, wherein the at least one further center pipe is arranged between the inner pipe and the outer pipe and, together with these, forms a multi-telescoping rod. In this way, it is possible to increase the telescoping length, without the length of the telescoping rod being increased when it is retracted.

BRIEF DESCRIPTION OF THE DRAWING FIGURES

Further advantages and features of the invention are apparent to a person skilled in the art from the accompanying figures and the detailed description of the exemplary embodiments.

FIG. 1 shows a first exemplary embodiment of the telescoping retractor receptacle to be supported on an operating table;

FIG. 2 shows a second exemplary embodiment of the telescoping retractor receptacle to be supported on an operating table;

FIG. 7 shows a seventh exemplary embodiment of the telescoping retractor receptacle comprising a fastening mechanism;

FIG. 8 shows a side view of a retractor receptacle;

FIG. 9 shows a side sectional view according to FIG. 8;

FIG. 10 shows a fastening mechanism and a fastening receptacle of the sixth exemplary embodiment in detail;

FIG. 11 is a schematic illustration of an operating table and thorax of a patient, and a telescoping retractor receptacle according to the seventh exemplary embodiment;

FIG. 12 shows a view of a patient on an operating table from above;

FIG. 13 shows a view of a patient on an operating table from the side;

FIG. 14 shows a perspective illustration of an eighth exemplary embodiment of the telescoping retractor receptacle comprising a fastening mechanism;

FIG. 15 shows a side illustration of the eighth exemplary embodiment of the telescoping retractor receptacle comprising the fastening mechanism;

FIG. 16 shows a perspective view of one variant of a detachable connecting means between the telescoping support rod and the retractor rod according to the present invention in the detached state;

FIG. 17 shows a perspective view of the variant of a detachable connecting means between the telescoping support rod and the retractor rod according to FIG. 16 in the operatively connected state;

FIG. 18 shows a side view of the variant of a detachable connecting means between the telescoping support rod and the retractor rod according to FIG. 16 in the operatively connected state.

DETAILED DESCRIPTION

Figures 3, 4:
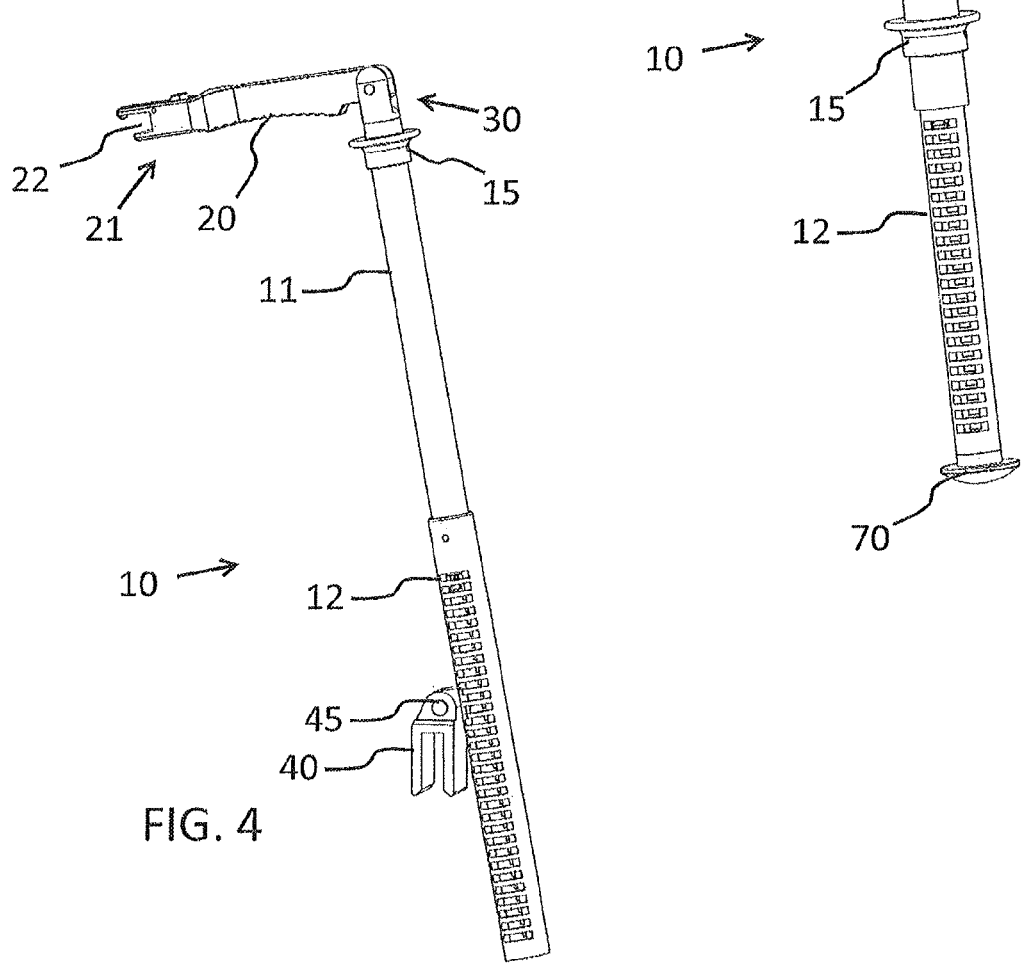
FIG. 3 shows a third exemplary embodiment of the telescoping retractor receptacle to be supported on an operating table.
FIG. 4 shows a fourth exemplary embodiment of the telescoping retractor receptacle to be supported on an operating table rail.

A first exemplary embodiment of the present invention is described in detail with reference to FIG. 1.

The telescoping retractor holder according to the first exemplary embodiment of the invention has a telescoping support rod 10, preferably comprising an inner pipe 11, an outer pipe 12, and a locking mechanism, and a retractor rod 20. The one, distal end of the retractor rod 20 comprises a retractor receptacle 21, which can releasably grip a retractor R. At the other, proximal end, the retractor rod 20 is operatively connected to the telescoping support rod 10 by way of a detachable/loose connecting means 30. According to this exemplary embodiment, the telescoping support rod 10 can be supported on an operating table O in that simply the free end of the outer pipe 2 (located opposite the connecting means) is positioned on the operating table O or placed in special indentations of the operating table O. The inner pipe 11 of the telescoping support rod 10 comprises an actuating mechanism 15, by way of which the locking mechanism can be transferred from a first position, in which the inner pipe 11 and the outer pipe 12 of the telescoping support rod 10 are held non-displaceably with respect to each other, into a second position, in which the inner pipe 11 and the outer pipe 12 of the telescoping support rod 10 can be moved relative to each other in the longitudinal direction of the pipes 11, 12. A certain amount of play exists between the inner pipe 11 and the outer pipe 12 such that the two pipes 11, 12 can be rotated with respect to each other about the respective longitudinal axis in a certain range.

The telescoping support rod 10 can be supported on the operating table O in an articulated manner by placing the telescoping support rod 10 on the operating table O. The actuating mechanism 15 is arranged directly beneath the joint connection 30 with the retractor rod 20 on the inner pipe 11. In this exemplary embodiment, the retractor receptacle 21 is adapted to positively grip a retractor R. For this purpose, the retractor receptacle 21 has a substantially U-shaped recess 22, into which a frame of a retractor R can be inserted, as shown in FIGS. 8 and 9. FIG. 11 shows that the retractor R is seated against the inside wall 23 of the recess 22 on three sides, and that the distal end of an elastically preloaded tongue 24 comprises a locking protrusion 25, which positively holds the retractor R in the U-shaped recess. The tongue 24 is rotatably attached on one side of the recess 22 and preloaded by a compression spring 26 so that the distal end of the tongue, comprising the locking protrusion 25, is pressed toward the recess 22. Moreover, the proximal end 27 of the tongue 24 comprises an actuating protrusion 28, which the surgeon can actuate or press so as to release the retractor R from the retractor receptacle.

In this exemplary embodiment, furthermore a hinged joint, preferably comprising a removable cotter bolt, serves as a quick-release fastener and forms the detachable connecting means 30 between the inner pipe 11 of the telescoping support rod 10 and the retractor rod 20. The actuating mechanism 15 is a ring here, which can be moved relative to the telescoping support rod 10 in the direction of the hinged joint 30 so as to transfer the locking mechanism from the first position into the second position.

The telescoping retractor holder according to this exemplary embodiment is used as following. After the surgeon has opened the sternum of the patient P and inserted and spread the retractor R, the surgeon grips the telescoping retractor receptacle in the region of the detachable connecting means 30 and places the telescoping support rod 10 on the operating table O. The surgeon then places the thumb on the detachable connecting means (hinged joint) 30 and uses the index finger and the ring finger to grip the ring 15, pulling the same in the direction of the thumb, so as to remove the lock in the telescoping support rod 10. The surgeon then adapts the length of the telescoping support rod 10 to the conditions of the patient P, which essentially means to the size of the thorax of the patient P. While continuing to hold the retractor holder in the region of the detachable connecting means 30 with one hand, the surgeon uses the other hand to guide the retractor receptacle 21 in the direction of the retractor R or of the intended fastening point on the retractor R. This is usually one of the two legs of a retractor, which run parallel to the sternum cut and carry the blades. The surgeon then inserts the retractor R in the retractor receptacle 21 by pushing the retractor receptacle 21 over the retractor R. The surgeon can now raise the side of the sternum of the patient P on which the retractor holder is positioned by again actuating the actuating mechanism and raising the detachable connecting means 30. However, since the retractor rod 20 is connected detachably, but rigidly to the retractor R, and thus forms a type of cantilever of the retractor R, a favorable lever is created for raising or exposing the one sternal half facing the support rod 10. In this way, the surgeon requires less force to expose the sternum. An added fact is that the ribs can be bent more easily (which is to say with considerably less force) to the outside than they can be bent into the chest. When the retractor rod 20 is raised, the ribs on the side of the retractor on which the telescoping retractor holder is attached are thus bent outward. This results in a force that tends to press the ribs on the other side of the thorax inward. The ribs, however, heavily resist such a deformation, whereby they essentially act as an abutment for exposing the opposing sternal half.

If the surgeon now lets go of the retractor holder, the retractor holder is supported on the operating table O, holding up the one sternal half. The above-described rotations a and 13, resulting from the mispositioning of the patient P and the differing nature of the caudal and cranial ribs, are compensated for by a rotation and slight tilting of the retractor receptacle.

If the surgeon, during the course of the operation, wants to raise the other side of the sternum of the patient P, the surgeon first brings the retractor R into an approximately horizontal position by adequately reducing the length of the telescoping support rod 10, detaches the retractor receptacle 21 from the retractor R, places the retractor holder on the other side of the patient P, fastens the retractor receptacle 21 to the other leg of the retractor R, and extends the telescoping support rod 10 again. The surgeon can carry out all these steps without leaving the sterile region. Skilled surgeons require only a single hand for the entire process, and will not have to use the second hand even once, to fasten the retractor receptacle on the retractor R or detach the retractor R from the retractor receptacle.

A second exemplary embodiment of the present invention is described hereafter with reference to FIG. 2. The second exemplary embodiment differs from the first exemplary embodiment only in the bearing plate 70 at the free end of the telescoping support rod 10. In the first exemplary embodiment, it is possible for the free end of the telescoping support rod 10 to slide when the friction between the telescoping support rod 10 and the operating table O is not sufficient or a person bumps against the retractor holder. So as to improve the bearing of the retractor holder on the operating table O, a bearing plate 70 is provided, which preferably has a spherical surface or spherical cap shape on the lower face. In this way, the retractor holder is less likely to slide.

A third exemplary embodiment of the present invention is described hereafter with reference to FIG. 3. The third exemplary embodiment differs from the second exemplary embodiment in that the inner pipe 11 forms the upper pipe, and the outer pipe 12 forms the lower pipe, in the second exemplary embodiment, while the inner pipe 11 forms the lower pipe, and the outer pipe 12 forms the upper pipe in the third exemplary embodiment. One alternative to the bearing plate 70 of the second and third exemplary embodiments, which is not shown, is a similar plate, the flat side of which is seated on the operating table O and which is attached to the free end of the telescoping support rod by way of a detachable ball joint.

A fourth exemplary embodiment of the present invention is described hereafter with reference to FIG. 4. The fourth exemplary embodiment differs from the second exemplary embodiment by a fastening receptacle 40, which in this particular case is attached to the side of the outer pipe 12 of the telescoping support rod 10. The fastening receptacle 40 is attached to the telescoping support rod 10 by way of a hinged joint 45 and has a U-shaped section, which fits on an operating table rail. To fit here shall mean that the fastening receptacle 40 makes contact with an operating table rail on three sides, while nonetheless being displaceable along the operating table rail. In addition, the telescoping support rod 10 is longer than in the preceding exemplary embodiments, so as to extend beyond the fastening receptacle 40, and consequently beyond the operating table rail, in the direction of the floor. The remaining design and the operating principle correspond to the first to third exemplary embodiments, wherein tilting of the retractor holder toward the patient P is made possible by the hinged joint 45, and tilting along the longitudinal axis of the operating table (angle β) is made possible by the telescoping support rod 10 rotating slightly with respect to the operating table rail, and wherein an incorrect position of the retractor R in the horizontal (angle α) can be compensated for by simultaneously displacing and tilting the fastening receptacle 40. The one-handed operation and one-handed repositioning from one side of the patient P to the other side work as in the preceding exemplary embodiments.

Figure 5:
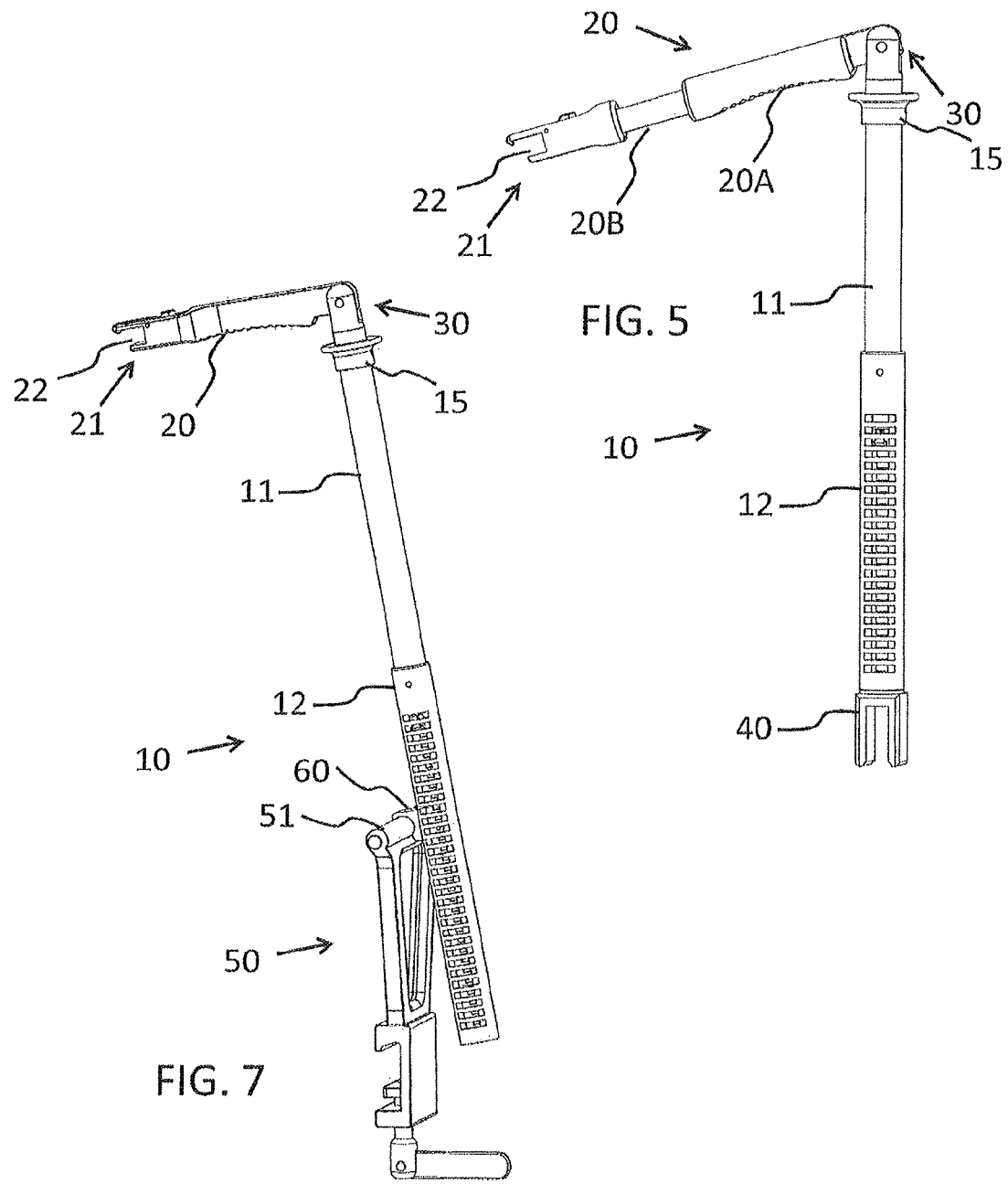
FIG. 5 shows a fifth exemplary embodiment of the telescoping retractor receptacle to be supported on an operating table rail.
Figure 6:
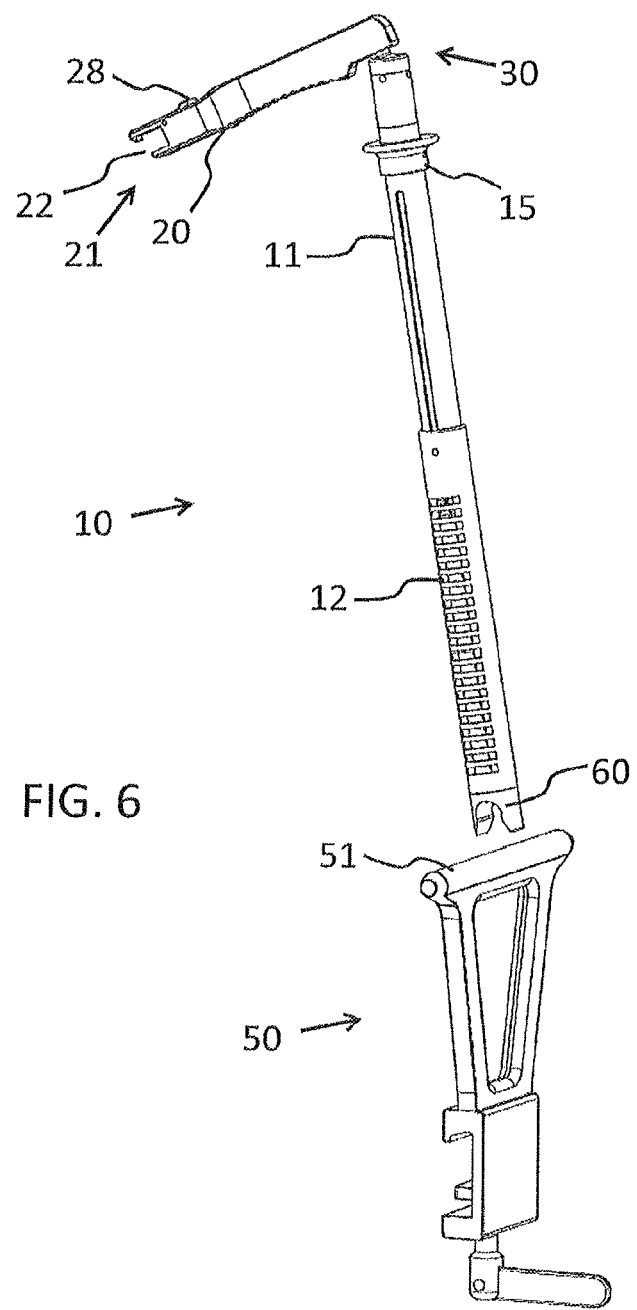
FIG. 6 shows a sixth exemplary embodiment of the telescoping retractor receptacle comprising a fastening mechanism.

A fifth exemplary embodiment of the present invention is described hereafter with reference to FIG. 5. This particularly advantageous exemplary embodiment differs from the fourth exemplary embodiment in that the fastening receptacle 40 is not attached to the telescoping support rod 10 in an articulated manner, but rigidly. Accordingly, the telescoping support rod 10 is not able to incline toward the patient P. When the surgeon raises one sternal half in one of the preceding exemplary embodiments by increasing the length of the telescoping support rod 10, this support rod would always incline toward the patient P (provided the same was stationary), since the length between the sternum and the detachable connecting means 30 between the retractor rod 20 and the telescoping support 10 was fixed. The location of the sternum in this case is the center between the two spread sternal halves, which is to say approximately the geometric center of the retractor.

However, if the telescoping support rod 10 is not able to incline toward the patient P when the support rod is extended, as is the case in this exemplary embodiment, the patient P would be pulled toward the telescoping support rod 10, which would be accompanied by considerable forces acting on the patient P and could cause traumatic injuries. In this exemplary embodiment, the retractor rod 20 is therefore designed to be freely telescoping, so that no lateral forces act on the patient P. The inner part 20B of the retractor rod 20 can be moved back and forth freely in the outer part 20A of the retractor rod 20 for this purpose across a sufficiently large range. Locking is not needed on the telescoping retractor rod 20; however, it may be advantageous for secure and space-saving storage. If the inner rod can be rotated with respect to the outer rod 20A in this telescoping retractor rod 20B, the rotation by the angle β can also be absorbed in this way.

A sixth exemplary embodiment of the present invention is described hereafter with reference to FIGS. 6 and 8 to 13.

This sixth exemplary embodiment shows a telescoping retractor holder comprising a telescoping support rod 10 having an inner pipe 11, an outer pipe 12, and a locking mechanism, and a retractor rod 20, which comprises a retractor receptacle 21 at one end. The retractor receptacle 21 is adapted to releasably and positively grip a retractor R and is identical to those of the preceding exemplary embodiments. The retractor rod 20, which has a fixed length, which is to say it is not telescoping, is attached at the other end to the inner pipe 11 of the telescoping support rod 10 by way of a detachable ball joint connection 30. An actuating ring 15, by way of which the locking mechanism is transferred from the blocking position into the release position, is attached just beneath the ball joint 30 on the inner pipe 11 of the telescoping support rod 10.

The telescoping retractor holder according to the sixth exemplary embodiment comprises a fastening mechanism 50, which has a fastening rail 51 and is adapted to be detachably fastened to an operating table rail 100 of an operating table O. In the present case, the fastening mechanism 50 is placed laterally on the operating table rail and clamped thereto by way of a screw. The outer pipe 12 of the telescoping support rod 10 comprises a fastening receptacle 60, which can be pushed onto the fastening rail 51 along the longitudinal direction of the fastening rail 51.

The fastening rail 51 has a cross-section that is composed of a substantially circular area 52 and a further area 53, wherein the other area is a circular segment area, so that the two areas together essentially correspond to the shape of a keyhole. The fastening receptacle 60 of the telescoping support rod 10 has a recess 61 having an inside wall 62 and two side walls 63, wherein the cross-section of the recess 61 substantially corresponds to the cross-section of the fastening rail 51, which is to say it also essentially has the shape of a keyhole. In addition, the inside wall 62 of the recess 61 establishes at least one undercut together with the fastening rail 51 when the fastening receptacle is slid on. In this way, tensile forces present in the telescoping support rod 10 can be transferred from the fastening receptacle 60 to the fastening rail 51 of the fastening mechanism 50. The side walls 63 of the recess 61 are spaced from the lateral surfaces 54 of the further area 53 of the cross-sectional area of the fastening rail 51 and oriented in such a way that a rotation of the telescoping support rod 10 relative to the fastening rail 51 is limited to a predetermined angular range, as is apparent in particular from FIGS. 10 and 11.

The angles and distances of the lateral surfaces 54 of the fastening rail 51 with respect to the side walls 63 of the fastening recess 60 as those shown in FIGS. 10 and 11 not only prevent the retractor holder from tilting away, but likewise prevent the retractor holder from falling onto the patient P. This means that the telescoping retractor holder, when pushed onto the fastening rail 51 of the fastening mechanism 50, can only rotate in a predetermined angular range with respect to the fastening rail 51. In this way, it cannot harm the patient P by tilting or falling on the same, it cannot tilt or fall out of the sterile region into the non-sterile, or at least not reliably sterile, region. If, additionally, the retractor receptacle 21 is fastened to the retractor R, the telescoping support rod 10 also can no longer inadvertently slide.

The operating principle of the present invention will be described again in detail based on this exemplary embodiment with reference to FIGS. 11 to 13. Two different procedures exist with the present exemplary embodiment.

The first procedure is very similar to the above-described procedures. For this purpose, the telescoping retractor holder comprises two fastening mechanisms 50, each of which is fastened on one side of the operating table on the operating table rails 100 prior to starting the surgery.

The surgeon initially opens the sternum of the patient P, inserts the retractor R, and spreads the sternum of the patient P using the retractor P. So as to expose, which is to say raise, one side of the sternum, for example so as to dissect free an artery running along the inside wall of the chest, the physician pushes the telescoping retractor holder onto the fastening rail 51 on the side of the sternal half to be raised. Subsequently, the surgeon fixes the retractor R to the retractor holder by way of the retractor receptacle 21. If the surgeon now wants to raise the side of the sternum on which the retractor holder is located, the surgeon will extend the telescoping support rod 10 using the one-hand actuating mechanism 15, whereby the retractor rod 20, together with the retractor R, becomes inclined. The distal leg of the retractor R is supported on the sternal half that is not to be raised, and the proximal leg of the retractor R pulls the sternal half to be raised upward.

After successfully conducting the work on this side of the patient P, the telescoping support rod 10 is shortened so much that the retractor receptacle 21 is substantially free of moment. In this state, the retractor R can be detached from the retractor R particularly easily and using only a single hand. The surgeon thus detaches the retractor R from the retractor receptacle 21 and pushes or pulls the telescoping retractor holder off the fastening mechanism 50 laterally in the longitudinal direction of the fastening rail 51. Subsequently, the surgeon pushes the telescoping retractor holder, without having to change grip, onto the fastening rail 51 of the second fastening mechanism 50 attached opposite the patient P, attaches the retractor receptacle 21 to the retractor R, which is to say to the opposing leg, as before, and is now able to again raise one half of the sternum, namely the other half of the sternum, using an extension of the telescoping support rod 10.

In this way, a surgeon is able to successively expose or raise the desired sternal half without the assistance of staff and without being exposed to the risk of entering the non-sterile region. In this first procedure, the surgeon has the advantage that the telescoping retractor holder is always arranged on the side of the patient P on which the sternum is being raised. The surgeon is expediently always located on the side of the sternal half that is not raised, since this provides the best visibility of the area to be dissected in the thorax of the patient P.

In the second procedure, the surgeon requires only a single fastening mechanism 50, which is fastened only on one side of the operating table O on an operating table rail 100 prior to starting the surgery.

The surgeon initially follows all the steps as with the first procedure, which is to say fixes the telescoping retractor holder to the fastening mechanism 50, fastens the retractor R to the retractor receptacle 21, and extends the telescoping support rod 10 so as to raise the half of the sternum on the side of which the retractor holder is arranged. If the surgeon now wants to raise the other sternal half, the surgeon does not have to be reposition the telescoping retractor holder to the other side of the patient P, but can simply shorten the telescoping support rod 10 beyond the state of the retractor receptacle 21 that is substantially free of moment. In this process, pressure is applied to the sternal half on the side of which the retractor holder is located. Since, as was already described above, ribs are more difficult to press in than they are to bend apart, the pressed sternal half essentially remains in the starting position (albeit spread apart, but not rotated, or raised or lowered), and the other sternal half is raised or exposed. While the telescoping retractor holder is located on the side on which also the surgeon is located in this case, the telescoping support rod 10 does not impede the surgeon during the surgery because it is drastically shortened. The forces exerted on the patient P are slightly greater when exposing a sternal half by shortening the telescoping retractor holder than when exposing it by extending the telescoping retractor holder; however, this is of no consequence for the majority of patients P. In this second procedure, the surgeon does not have to reposition the telescoping retractor holder, saving both a fastening mechanism 50 and the time for the repositioning.

A seventh exemplary embodiment of the present invention is described hereafter with reference to FIG. 7. The seventh exemplary embodiment differs from the sixth exemplary embodiment in that the fastening receptacle 60 is not arranged at the free end of the telescoping support rod 10, but is attached to the side of the telescoping support rod 10, or more specifically on the outer pipe 12. Moreover, a detachable hinged joint 30, comprising an easily removable cotter bolt, for example, is provided between the retractor rod 20 and the telescoping support rod 10, instead of a ball joint.

Further advantages of the invention or of individual exemplary embodiments of the invention are described hereafter.

The use of one or more fastening mechanisms 50 also has the advantage that the surgeon, when using the fastening rail 51, does not run the risk of damaging other operating materials. If the surgeon were to support the telescoping retractor holder directly on the covered operating table rail, the surgeon would not know whether the support point is free from cables, tubing or optical fibers, which could be hidden beneath the drapes covering the operating table O and could become disconnected.

FIG. 10 shows the geometry of a fastening receptacle 60 and a fastening rail 51. The protrusions provided at the transitions from the inside wall 62 to the side walls 63, 63 form undercuts with the transition of the peripheral surface 55 to the lateral surfaces 54, 54 of the fastening rail 51. As is apparent from FIG. 10, the lateral surfaces 54, 54 are parallel to each other, while the side walls 63, 63 from a certain angle between each other. In this way, a certain freedom of movement of the telescoping support rod 10 around the fastening rail 51 exists, which allows an adaptation to the variable geometry of the telescoping retractor holder during use. At the same time, the side walls 63, 63 limit a rotation of the telescoping support rod 10 around the fastening rail 51, so that the upper region of the telescoping support rod 10 cannot tilt into the non-sterile region, and also cannot tilt onto the patient P. The angles of the two side walls 63, 63 need not be symmetrical to the longitudinal axis of the telescoping support rod 10, but may be established as needed.

So as to simplify lateral pushing of the fastening receptacle 60 onto the fastening rail 51, the fastening rail can be tapered at one end or at both ends. This simplifies pushing on, in particular in one-hand operation. In addition, the surgeon is not tempted to grab the telescoping support rod 10 in the region of the fastening receptacle 60, which is to say in the non-sterile region.

The fastening receptacle also does not have to be open toward the free end of the telescoping support rod 10, but may be arranged at an arbitrary angle with respect to the longitudinal axis of the telescoping support rod 10. For example, the fastening receptacle 60 may be open transversely to the longitudinal axis of the telescoping support rod 10 toward the operating table O, and the fastening rail may be arranged rotated 90°, pointing away from the operating table O.

Moreover, a three-piece or multi-piece telescoping mechanism may be used in the telescoping retractor holder, instead of a two-piece telescoping mechanism. The inner pipe 11 may be rotationally fixed with respect to the outer pipe 12, but may also be rotatable within a certain range.

FIGS. 14 to 19 show an eighth exemplary embodiment of a retractor holder according to the invention. Contrary to the above-mentioned exemplary embodiments, the operative connection between the retractor rod (retractor lever) 20 and the support rod (support) 10 is not implemented by a detachable hinged or ball joint here, but by a loose hooking mechanism.

In detail, the support rod 10 according to FIGS. 14 and 15 is composed of the inner pipe 11, which now takes on the form of a spindle and is mounted axially movably and rotatably in the outer pipe 12 in the form of a receiving cylinder. A knurled nut 80, which is axially supported on an end face of the receiving cylinder 12, is screwed onto the spindle 11. Moreover, still another latching engagement (not shown in detail) that can be released manually, such as by way of a lever 81, can be provided on the receiving cylinder 12 and used to quickly release the spindle 11 so as to remove the same from the receiving cylinder 12, for example to be able to clean the individual segments of the support 10.

Figure 19:
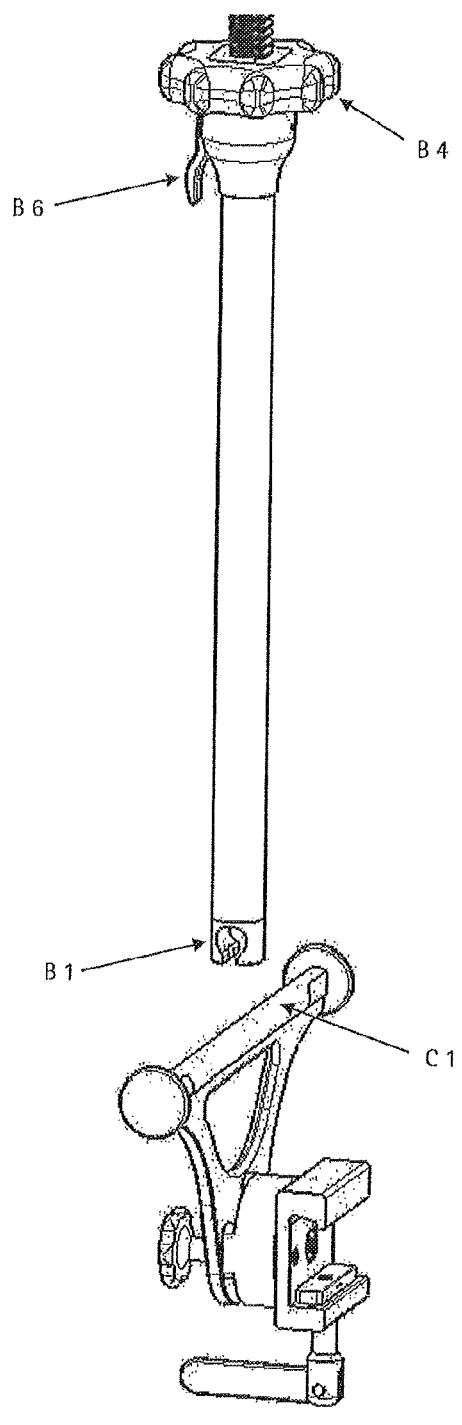
FIG. 19 shows a further variant of a support rod comprising a fastening receptacle according to the principle of a spindle.

The fastening mechanism 50 for fixing the telescoping retractor holder on an operating table or similar platform is provided at the one (lower) end of the support rod 10, as is shown in particular in FIG. 19. As was already described above, the fastening mechanism 50 comprises a dedicated separate unit in the form of a manually actuatable clamp or bar clamp 82 for the fixation to the operating table, on which a fastening rail 51 is mounted, preferably pivotably/rotatably and lockably. The support rod 10, in return, has a fastening receptacle 60 at the lower end or end section, which can be prompted to engage with the fastening rail 51, preferably in a hinge-like manner.

As is illustrated in particular in FIGS. 16 to 18, a U- or fork-shaped bearing element 83 is arranged on the opposing (upper) end of the support rod 10 such that the two legs of the bearing element 83 extend in parallel to each other and axially with respect to the support rod 10. The two legs are connected to each other by a cross pin 84. As an alternative, however, it is also conceivable to integrally form a transverse edge or strip at the upper end of the support rod, which would then correspond to the cross pin, and to provide or design the transverse edge with end stops at the respective edge longitudinal ends.

As is also shown in particular in FIGS. 16 to 18, the proximal end section of the retractor rod 20 has a number of axially spaced points of engagement/points of action 85 in the form of annular ridges or grooves, whereby a corresponding number of (radial) undercuts is formed. In other words, no bearing lugs are formed in the retractor rod 20 in this exemplary embodiment, but radially freely accessible undercuts, in which the cross pin 84 or cross strip on the support rod 10 can be inserted in the transverse direction of the cross pin or cross strip. It shall be pointed out that a type of bearing lug that is not closed in the circumferential direction in a clamp-like manner, but is slotted, may also be formed on the retractor rod 20, whereby in this case the cross pin 84 or cross strip can also be latched/clipped in the transverse direction of the same.

The undercuts thus prevent the retractor rod 20 from longitudinally sliding off the cross pin 84 at the selected point of action, and the two legs prevent the retractor rod 20 from sliding transversely off the cross pin 84. Moreover, the undercut continues to allow the retractor rod 20 to pivot in a hinge-like manner about the cross pin 84, wherein, however, the operative connection between the two components, these being the retractor rod 20 and the support 10, is achieved by free/loose bearing thereon.

The overall system of the lifting device according to the invention, which is to say of the telescoping retractor holder, consequently is essentially composed of the three different separate, which is to say detachably connected/connectable, main components:

For one, it is composed of a part consisting of the retractor lever 20 comprising the adaptation unit 21 for the retractor, a second part, namely the so-called support 10, which represents a height-adjustable device, and a third part, which forms the adapter (fastening mechanism) 50 for the operating table rail onto which the rail 10 is placed.

The operating table is covered with sterile drapes already before the surgery when preparing the operating equipment. The table adapter (fastening mechanism) 50 is then fastened to the operating table rail, whereby the problem of sterile attachment and repositioning is circumvented. The adapter 50 itself is now sterile, and the support 10, which is placed thereon, does not protrude into the non-sterile region beneath the operating table plane. If both mammary arteries in the thorax of the patient are to be dissected, a respective adapter 50 is attached on either side of the operating table. The support 10 may then be repositioned in a sterile manner from one to the other adapter 50 by releasing the clamp 82.

Then the surgery begins, initially without use of the retractor lever 20 or the support 10, by cutting the sternum and inserting the retractor. For the dissection of the mammary arteries, the surgeon now places the support 10 onto the fastening rail 51 of the table adapter 50 located on the table side opposite the surgeon. The surgeon then adapts the retractor lever 20 to the retractor receptacle 21 comprising the retractor in such a way that the free proximal end of the retractor lever 20 points in the direction of the support 10. The two described work steps function solely by simply placing or pushing the retractor receptacle 21 on the retractor, as was already described above.

Since the table adapter 50 itself comprises the fastening rail 51 in the present exemplary embodiment, which extends or can be oriented above and in parallel to the table rail, the surgeon has sufficient leeway to compensate for the longitudinal offset between the table adapter 50 and the retractor, which results from the size and position of the patient. This rail 51, in cooperation with the positive adaptation point/fastening receptacle 60, orients the support 10 as vertically as possible, so that the same is securely positioned and cannot fall into the operating area. Another advantage is that the surgeon, when using the rail 51 as the adaptation point, does not run the risk of damaging other operating materials.

After the retractor lever 20 is connected to the retractor and the support 10 to the table adapter 10, the height of the support 10 is adjusted upward to a certain degree using the actuating element/hand wheel/knurled nut 80. In the present exemplary embodiment, this is carried out by way of the threaded rod 11 in the telescoping pipe 12 and the nut 80, which is designed as a relatively large actuating element. Using the retractor lever 20, which subsequently is loosely placed vertically onto the cross pin 84 on a selected point of action 85, the retractor can be raised on one side; thanks to the physically good lever conditions, this can be done very smoothly. The free, proximal end of the retractor lever 20 is then inserted into a provided point of action 85 on the cross pin 84/cross strip at the upper end of the support 10, wherein the point of action 85 is designed in an undercut manner, so that the retractor lever 20 cannot slide to the side or off the cross pin 84 in the longitudinal direction. The support 10 can now be adjusted further so as to increase the length thereof, which due to the spindle drive takes place with considerably more finesse than mere raising by hand, until optimal visibility of the artery for the surgeon has been established. The support 10 of the retractor is then located obliquely with respect to the starting position of the same.

If the surgeon is familiar with this system, subsequent adjustment may be dispensed with, since the appropriate height of the support 10 was already preset prior to connecting the retractor lever 20 to the support 10.

Another option for use of the system is to attach/place the retractor lever 20 on a support having a height that has not yet been adjusted, still being at the minimum height of the same, and to then bring about the oblique position of the retractor only by way of the actuating element 80. As a result of the separation of the support 10 and retractor lever 20 into two parts according to the invention, and the loose/detachable connection between these, the surgeon can also work very flexibly and individually.

So as to carry out the raising and subsequent holding of this exposed position of the sternum as atraumatically as possible for the patient, no fixed, lockable or form-locked connection exists between the retractor lever 20 and the support 10. In this way, a certain angular offset between the retractor lever 20 and the support 10 in any plane can be compensated for, without resulting in negative effects on the patient. The longitudinal axis of the support 10 is always substantially vertical, whereby no space outside the operating table surface is taken up. Moreover, the support 10 is not considerably taller than the obliquely positioned retractor, which represents another advantage over the other systems comprising external fastening means.

In the described variant embodiment according to the eighth exemplary embodiment of the present invention, the spindle thread for height adjustment could also be replaced with a toothed rack and a corresponding crank mechanism. Moreover, the support 10 can be designed as a multi-piece telescope, as in the above-described exemplary embodiments, so as to create a lifting height that is greater than the first individual element. In this way, it would be possible to collapse all elements inside each other in a very compact manner, yet also to be extended to a large height.

As was already indicated above, a small actuating element 81 was optionally provided between the individual segments 11, 12 of the height-adjustable support 10 so as to be able to disassemble the segments 11, 12 and clean these better. In the assembled state, this element 81 prevents the user from accidentally pulling the segments 11, 12 apart. Finally, another variant embodiment could dispense with the entire table adapter 50, and the support 10 could be placed directly on the operating table rail or on other holding devices in the operating area.

The proximal end of the retractor lever 20 can be designed as an ergonomic handle (comprising one or more points of action 85 at the free end of the handle), or can comprise only the points of action (detent positions) 85 for inserting the counterpiece (cross pin 84) of the support 10.

Ideally, the retractor lever 20 consequently does not comprise any fastening or actuating elements whatsoever, but may be joined to the mating shape of the retractor purely by positive fit, for example by simple pushing or plugging.

Further combinations of the individual features are possible, and numerous further modifications and variants will be apparent to a person skilled in the art from the present description and the accompanying claims and figures.

The invention claimed is:

1. A retractor holder for supporting a surgical retractor during surgery, the retractor holder comprising:
    a support rod having a first end, a second end, and an actuating element between the first end and the second end for adjusting a length of the support rod;
    a fastening mechanism attached to the first end of the support rod for fixing the support rod to an operating table or platform;
    a bearing element attached to the second end of the support rod, the bearing element comprising a rounded cross member, the cross member defining a transverse axis longitudinally through the cross member; and
    a retractor rod comprising a circumference and defining a plurality of annular grooves, the annular grooves extending around the circumference and axially divided from one another by a plurality of ridges, the retractor rod further defining a longitudinal rod axis through the retractor rod,
    the cross member defining a convex bearing surface, and each annular groove of the retractor rod defining a concave bearing surface,
    the retractor rod balanced by gravity on top of the cross member and distributing its entire load to the cross member, with the concave bearing surface of one of the annular grooves contacting the convex bearing surface of the cross member,
    such that the retractor rod is pivotable about the transverse axis and rotatable about the rod axis at a selected point of action on the retractor rod, while remaining fixed against translation relative to the cross member.

2. The retractor holder of claim 1, wherein the cross member comprises a cross pin.

3. The retractor holder of claim 1, wherein the bearing element comprises a first leg attached to a first end of the cross member, and a second leg attached to a second end of the cross member, the first and second legs preventing the retractor rod from sliding transversely off the cross member.

4. The retractor holder of claim 1, wherein the support rod comprises an inner rod telescopically received in an outer rod, and the actuating element is operable to adjust an axial position of the inner rod relative to the outer rod to adjust the length of the support rod.

5. The retractor holder of claim 4, wherein the support rod further comprises a release lever operable to release the inner rod from the outer rod and allow removal of the inner rod.

6. The retractor holder of claim 4, wherein the inner rod comprises a threaded rod and the outer rod comprises a telescoping pipe.

7. The retractor holder of claim 6, wherein the actuating element comprises a nut that is screwed onto the threaded rod and rotatable to adjust the position of the telescoping pipe relative to the threaded rod.

8. The retractor holder of claim 1, wherein the annular grooves are radially accessible undercuts into which the cross member can be inserted.

9. The retractor holder of claim 1, wherein the fastening mechanism comprises a clamp.

10. The retractor holder of claim 1, wherein the plurality of ridges are cylindrical.

11. The retractor holder of claim 1, wherein the retractor rod comprises a retractor receptacle for gripping a retractor.

12. The retractor holder of claim 11, wherein the retractor rod comprises a proximal end and a distal end opposite the proximal end, the retractor receptacle being located at the distal end.

13. The retractor holder of claim 12, wherein the annular grooves are formed on the proximal end.

14. The retractor holder of claim 12, wherein the retractor rod is supported on the cross member with the proximal end elevated above the distal end.

* * * * *